United States Patent [19]
Sertich

[11] 4,320,927
[45] Mar. 23, 1982

[54] DENTAL DRILL WITH MAGNETIC AIR TURBINE HAVING MAGNETIC BEARINGS

[76] Inventor: Anthony T. Sertich, 30 Dover Green, Staten Island, N.Y. 10300

[21] Appl. No.: 132,512

[22] Filed: Mar. 21, 1980

[51] Int. Cl.³ .............................................. F16C 39/06
[52] U.S. Cl. ......................................... 308/10; 308/9; 433/120
[58] Field of Search ................. 308/10, 9; 433/120, 433/130–133

[56] References Cited
U.S. PATENT DOCUMENTS

| | | | |
|---|---|---|---|
| 3,493,275 | 3/1970 | Stone | 308/10 |
| 3,900,952 | 8/1975 | Landgraf | 433/133 |
| 3,958,842 | 5/1976 | Telle | 308/10 |
| 4,072,370 | 2/1978 | Wasson | 308/10 |
| 4,128,280 | 12/1978 | Purtschert | 308/10 |
| 4,153,993 | 5/1979 | Kataoka | 308/10 |

*Primary Examiner*—R. Skudy

[57] ABSTRACT

In a preferred embodiment, a magnetic air turbine dental drill having bearing function is achieved by spaced-apart annular magnets having therebetween in spaced-apart relationship an intermediate annular third magnet with the magnetic poles of the three magnets aligned coaxially and with magnetic poles of the intermediate third magnet being positioned in opposing like-pole repelling relationships to spaced-apart juxtaposition poles of the first and second magnets, and the third magnet as an annulus having upper and lower concavely shaped faces substantially seated in a lower convex face of the first magnet of annulus shape and in an upper convex face of the second magnet of annulus shape, third magnet being fixedly mounted onto and revolvable with a coaxially aligned shaft extending through the apertures of the first and second annuluses in spaced-away relationship therefrom, resulting in angular opposing faces of the magnets exerting both axial and transverse stabilizing forces in stabilizing the shaft, utilizing cobalt magnets.

9 Claims, 4 Drawing Figures

DENTAL DRILL WITH MAGNETIC AIR TURBINE HAVING MAGNETIC BEARINGS

This invention relates to a very minutely-sized air-turbine drill having improved bearing suspension of the drive shaft.

BACKGROUND OF THE INVENTION

A primary controlling factor with regard to the present invention is the need for miniature operative elements, for use in dental drill technology, recognizing that the dental drill not only has to be held comfortably and firmly within the hand or fingers of the dentist, but to a large extent has to be of sufficiently small size as to be placed virtually within a dental patients mouth with room to spare in order to manenuver as required during a drilling procedure. Accordingly, it is not only undersirable but unthinkable to have practically a device having numerous large elements in the making-up of the structure of a dental drill.

It is thus accordingly noted that the present invention is not the first to recognize the need for both forces parallel to the shaft axis and transverse to the shaft axis. Nor is the present invention the first to utilize the concept of magnets to achieve such forces for stabilizing the shaft against axial and transverse-plane movement. For example, U.S. Pat. No. 4,128,280 granted December 1978 to Purtschert in its FIGS. 1, 3, 4, 7 and 8 illustrated multiple magnets having opposing poles to prevent lateral movement of the shaft in a direction of a plane transverse to the axis of the shaft, and FIGS. 5 and 6 illustrate other plurality of magnets placed with opposing repelling poles to stabilize against movement of the shaft axially responsive to outside forces and while the shaft is rotated by its drive; in likewise opposing repelling facing of like-poles to prevent axial movement of the shaft, there is FIG. 4 of U.S. Pat. No. 4,153,993 to Kataoka et al. There are other even less relevant patents such as the radial bearing magnets of U.S. Pat. No. 3,958,842 to Telle, and of U.S. Pat. No. 4,072,370 to Wasson. There is the multiple magnets vertical suspension system also of Stone et al. of U.S. Pat. No. 3,493,275. In the Stone et al. patent, as is the situation in the Purtschert patent, there are separate pairs of patents to achieve the separate functions, namely one set of patents to prevent movement of the shaft in axial directions, and an additional set of magnets to prevent movement of the shaft laterally, i.e. transversly of the longitudinal axis of the shaft. Such patent typify the above-noted undesirable utilization of a plurality of elements to achieve the total bearing function, with a result of a very large machine of a size that would be totally unsuitable for miniature requirements of a dental drill of optimum small size; such problem is compounded because the magnets utilized in these patents not only require the plurality of sets of magnets, but the permanent magnets in order to exert sufficient force to stabilize properly and to a minimum required degree for a high-speed drill and high pressures to which a dental drill is subjected, must be of sizes factually much larger acknowledged or shown in the preceding noted prior art patents. That is to say, there is no way that miniature permanent magnets shown in those patents would work with sufficient power, and to use sufficiently large magnets would render the combination unthinkable too large for use in dentistry.

On the other hand, there truly has heretofore existed a great need for an improved dental drill hopefully devoid of the vibration problem and wearing ball bearings that are still utilized conventionally in even the latent dental drills, for reason of lack of any satisfactory alternative practically workable. More particularly, the modern air turbene drills are very high speed drills with the result that the bearings have only a limited life, such being a very costly matter, as well as bothersome problem. Dentist have sufficient problems to be concerned with without having to worry about the bearings of the drill.

SUMMARY OF THE INVENTION

Accordingly, objects of the present invention the obtaining of an improved and more efficient magnet-bearing suspension for a dental drill or for any other friction-free bearing in the industrial field.

More particularly, it is an object is additionally to obtain a high-powered and more compact magnetic bearing suspension unit employing fewer elements and more efficiently in the miniature dental drill technology.

Another object is to provide a novel magnetic unit that concurrently stabilizes against both axial movement and transverse movement of a dental drill shaft, or other driven rotatable shaft.

Another object is to provide a new and improved air-turbine drill for dental drill technology having lengthened longevity of overall motor elements, as a result of the novel magnetic bearing unit a part thereof.

Other objects become apparent from the preceding and following disclosure.

One or more objects of the invention are obtained by the invention as typically represented by the illustrative figures intended solely to improve understanding but not to unduly limit the invention.

Broadly the invention may be described as a magnetic bearings device inclusive of a support structure having mounted thereon spaced-apart first and second magnets in substantially axial alignment with unlike poles adjacent, and having a third magnet located therebetween and axially-aligned with the first and second magnets with like-poles in opposing relationships and with the third magnet mounted on a shaft, the improvement arising from opposing faces of the first and third magnagnets being substantially parallel to one-another and both of the opposing faces being of shapes that the respective faces each extend substantially along a plane transverse and at a significantly severe angle to a perpendicular from a longitudinal axis of the respective magnets, perferably ranging from about 15 to 35 degrees, and more preferably from about 20 to 25 degrees, and likewise for the opposing faces of the second and third magnets, with the result that there is provided magnetic stabilizing forces acting against both transverse and longitudinal movement relative to axes of the respective magnets. In the illustrated embodiment, a preferred arrangement, the first, second and third magnets are each in the form of an annulus with the magnetic poles being at the top and bottom of the annulus, and with the faces being angled to form a depressed center or concave center, or alternatively a raised center or convex center, with opposite end faces of the third intermediate magnet spaced-apart from but nested with the opposing faces of the first and second magnets, the intermediate third magnet being mounted around and revolvable with the shaft that extends through the aperatures of the first and second magnets in their annulus forms. It is virtually immaterial which of opposing faces is convex and which is concave.

For purposes of the illustrated preferred embodiment of a dental drill or other very small motor device, in this case the minutely sized dental drill, the required magnets in order to be both of a necessary compact nature and high-powered of a magnitude necessary to withstand the high-speed torques and the axial and transverse or lateral pressures, must be the rare-earth cobalt high energy permanent magnets, the ones being used by the inventor being the rare-earth cobalt high energy permanent magnet. The more preferred dental drill as here illustrated is utilizing a magnetic air turbine motor having the novel magnetic bearings of this invention as a part thereof.

In a more preferred embodiment, as in the presently illustrated air turbine magnetic-bearing drill, there are also mounted therein ball-bearing rings in a spaced-away relationship from the revolvable shaft as a safety feature to prevent an accidental wearing of adjacent faces if and when lateral and/or axial force(s) on the rotatable shaft exceed the stabilizing magnetic forces, such that the bearings would come into contact with the shaft prior to such damaging or wearing contact.

Except as a part of a preferred combination working for high speed rotation where wear of bearings and vibrations are major problems, as previously noted, and therefore the novel magnetic bearings giving a new result for such turbine embodiment, the invention is not otherwise in the mechanics of the turbine which is conventional technology.

In a preferred embodiment, the magnetic mass of the third magnet includes the mass of the turbine flanges which are carved-out of the circumscribing surface of the third magnet. Such arrangement permits a maximum of both magnet mass and magnetic power for the third magnet.

THE FIGURES

FIG. 1 is a diagramatic in-part view of a dental drilling apparatus, showing in substantial entirety the air turbine drill motor and drill mounted thereon, shown in varying degrees of cross-section and cut-away, for improved illustration, and further showing the planes of cross-section for other Figures FIG. 2 illustrates four different cross-sectional views as taken along lines 2a, 2b, 2c and 2d of FIG. 1, all views being diagrammatic and not intended to be to actual scale.

DETAILED DESCRIPTION OF THE INVENTION

Figure 1:
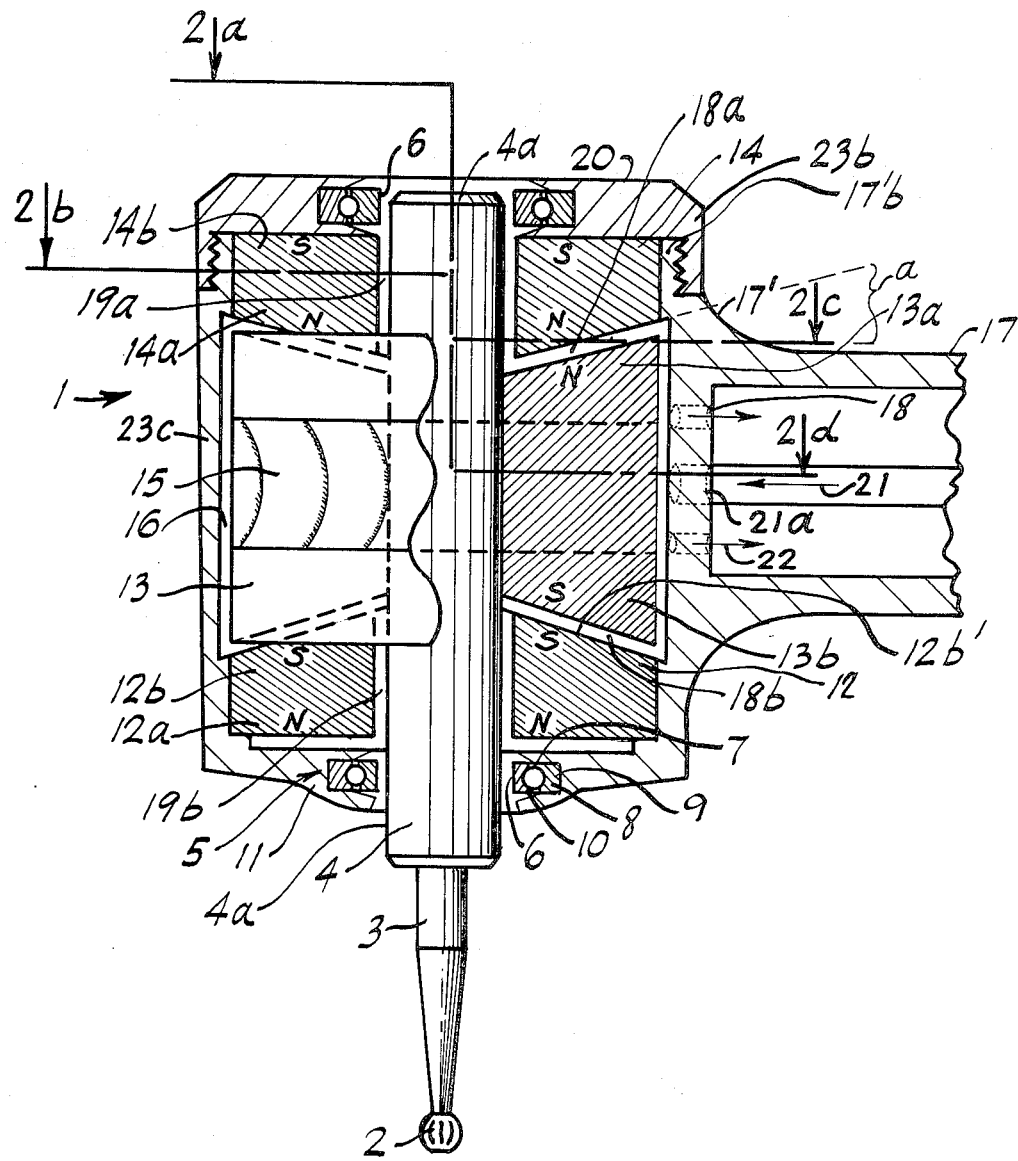
Figure 2:
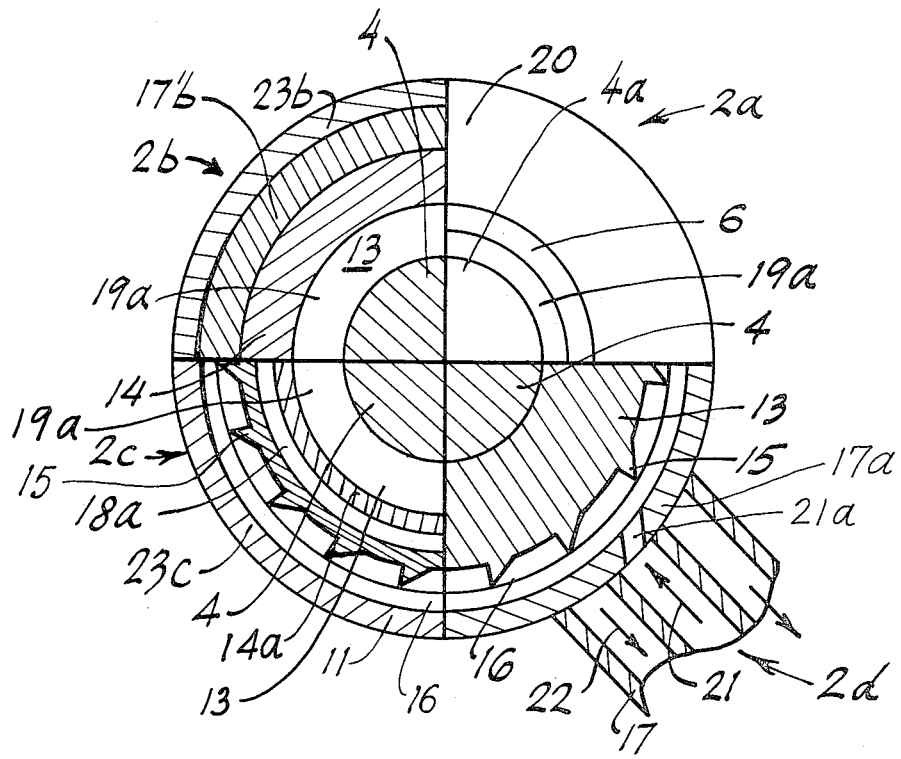
Figures 3, 4:
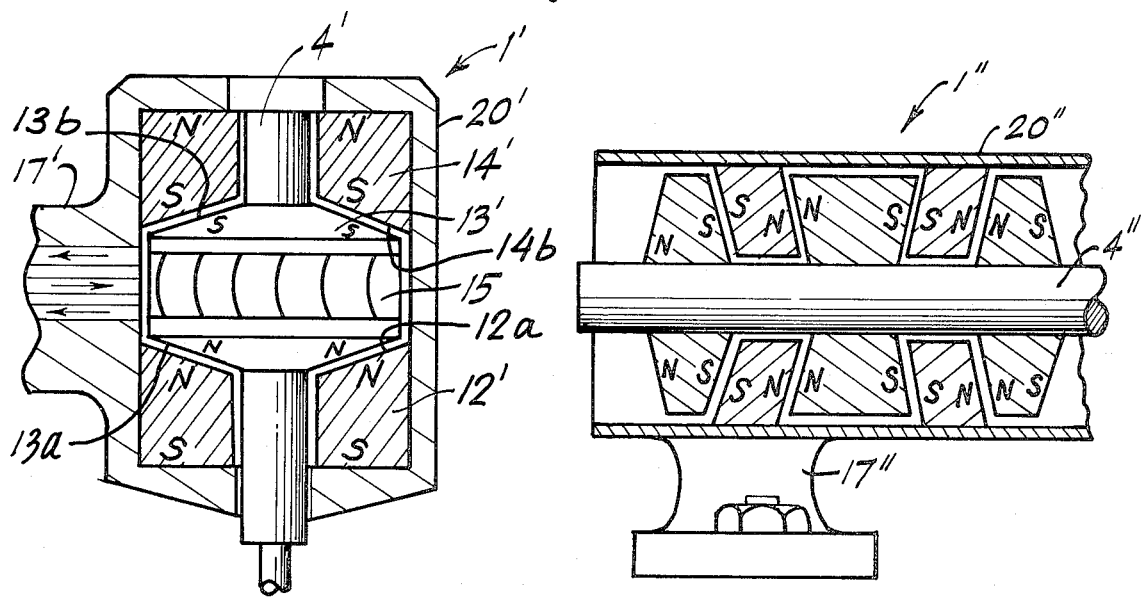
FIG. 3 illustrates an alternate representative embodiment of the invention shown merely diagrammatically in cross-sectional view.
FIG. 4 illustrates an alternate representative embodiment of the invention shown merely diagrammatically in cross-sectional view.

In greater detail, FIGS. 1 and 2 represent a common embodiment, and FIGS. 3 and 4 represent different embodiments having contemplated alternate variations in shapes of the magnets in both FIGS. 3 and 4, and in FIG. 4 illustrating additional annulus magnets also co-axially arranged, some mounted on the support structure or housing, and others mounted to revolve with the revolvable shaft. The FIG. 3 embodiment represents an embodiment likewise driven by an air turbine, while the FIG. 4 embodiment represents by cut-away portion thereof, any suitable drive for the driving mechanism of the shaft 4" thereof.

Accordingly, the operation is best explained by reference to FIGS. 1 and 2 in the following description.

In FIG. 1 may be seen a dental drill device 1, including a drill 2 on its mounted chuck 3 mounted within the shaft 4. There are many conventional mechanisms of mounting such chuck onto the shaft, and such does not constitute the present invention except as a conventional technology mounting. The accessory or safety bearings 5 at each of opposite ends of the shaft 4 spaced-away from and circumscribing the shaft 4, include the outer ring 9 mounted on the support housing 20, and the inner ring 6, each of the inner and outer rings having concave surfaces between which the ball bearings 8 are mounted in contact with the concave surfaces 7 and 10 at aperature-forming structure 11, for example.

Mounted within the housing support 20 are the annular magnets 12 and 14. Spaced therebetween is the intermediate annular magnet 13, having its north and south faces spaced-away from the like-pole faces of the magnets 12 and 14; The intermediate annular magnet 13 is fixedly-mounted on the shaft 4, i.e. is affixed to the shaft so that the magnet 13 and shaft 4 revolve as a single unit together when air impels against the turbine flanges 15 thereby causing the shaft 4 to revolve. The annular magnet 14 has north pole 14a and south pole 14b; the annular magnet 12 has north pole 12a and south pole 12b; and the annular magnet 13 has north pole 13a and south pole 13b. North pole or face 14a opposes and repels north pole 13a, and south pole 12b opposes and repels south pole 13b. It must be noted that the heart of the invention lies in the respective opposing faces of these above-noted poles being at an angle relative to a right-angle transverse plane transverse to a longitudinal axis of the shaft 4, whereby there is achieved repelling force which have both laterally-transverse and up-wardly and downwardly-longitudinal vector forces acting on the shaft to thus stably hold the shaft 4 steady against both axial and transverse forces, relative to the shaft 4; preferably the number of degrees of the respective angles of incline on the face of the various magnets, as typically represented by angle a of FIG. 1, is within the broad or narrow ranges previously set-forth above as obtaining the maximum repelling and thus stabilizing forces.

The turbine flanges 15 are driven within the turbine space 16 by air traveling in air tube 17 toward the flanges 15 through the air inlet 21a in structure 23c of the housing 20, and exiting through the air outlets 18, in conventional air turbine manner and mechanism of operation.

The repelling forces of the magnetic bearings of the present invention maintain the spaced-relationships of the gaps 18a and 18b and 19a and 19b.

Turbine inlet air travels in direction 21 and outlet air travels in direction 22.

Typically the housing 20 is assembled by a screw-on cap-portion inclusive of female-threaded lip 23b and male-threaded lip 17'b of handle and air-tubing joining structure 17'.

It should be noted that the opposing magnets' faces on opposite sides of the gaps 18a and 18b are substantially parallel to each other; the annular face of south pole 12b and the annular face of north pole 14a are each convex and circumscribing of the space 19b and the shaft 4, in the embodiment of FIGS. 1 and 2. Likewise, the north pole 13a and the south pole 13b are each concave.

The numerals of FIG. 2 are the same as noted-above for the FIG. 1 illustration. FIG. 2 has the beneficial effect of showing the typical shape of the various elements, and better illustrating their relative position one to the other, noting however that the Figures is not intended to be exactly to scale nor an engineering drawing. The air outlets are not normally aligned with the air inlet, and thus FIG. 2 does not show the air outlets in the plane of this cross-sectional view of view 2d. The FIG. 2 shows cross-sections at three different points, and an end view. The end view taken at FIG. 1 line 2a is shown in the quardrant 2a of FIG. 2; the cross-sections of lines 2b, 2c, and 2d respectively, are shown at the quardrants 2b, 2c, and 2d of FIG. 2.

FIG. 3 is intended to illustrate an alternate embodiment in which the first and second magnets 14' and 12' are the opposing ends of the mounted patents, relative to the intermediate magnet, and the faces of the magnets 14' and 12' are both here concave, rather than convex (FIG. 1); and likewise, the faces of the magnetic poles 13a and 13b are convex, rather than concave. Also it will be noted that in this FIG. 4 embodiment, as compared to the FIG. 1 embodiment, the polarities of the magnets have been reversed. The significant points are that the faces in opposing relationships are like-poles and are angular relative to a transverse plane perpendicular to a longitudinal axis of the shaft 4'.

FIG. 4 is further representative of a shaft 4" driven by any appropriate or conventional driving mechanism, together with the utility of the present inventions magnetic bearings utilizing a series of annular magnets having the same relative relationships as set-forth in the preceding FIGS. 1, 2 and 3, illustrating that also a plurality of magnets may be utilized within the scope of the invention. As with prior embodiments, the significant features are the presence of repelling opposing poles with each opposing repelling poles' face being angular as above-described and being substantially parallel to the opposing face thereto, for maximum force of repulsion and stabilizing effect.

For the embodiments of FIGS. 3 and 4, it is to be understood that the corresponding "primed" numbers such as 4' and 4" and the like, correspond to originally identified elements such as the shaft 4.

It is within the scope of the invention to make such variations and modifications as would be apparent to a person skilled in this art.

I claim:

1. A magnetic bearing unit comprising in combination: a support structure; at least two spaced-apart magnets in the form of first and second annuluses coaxially aligned and both mounted fixedly onto said support structure, the magnets of said first and second annuluses having unlike magnetic poles facing one-another for annulus faces in juxta-position spaced-apart relationship, as a first annulus face of said first annulus and as a second annulus face of said second annulus; and a third magnet in the form of a third annulus mounted around and fixedly onto an elongated shaft, the third annulus being coaxially aligned with said first and second annuluses and positioned between said first and second annuluses in spaced-away relationship from both the first and second annuluses with said shaft extending through a least an aperature of one of said first and second annuluses axially thereof and in spaced-away relationship from the annulus inner wall, said third magnet having like-magnetic poles adjacent in relationship to adjacent said first and second annulus faces such that each of said first and second annuluses are repelled magnetically by the magnetic forces of said third annulus; said third magnet having a third face in opposing magnetic relationship to said first annulus face and having a fourth face in opposing magnetic relationship to said second annulus face in said relationship of magnetically repelling said first and second annuluses; at least one set of (1) said first and second annuluses faces, and (2) said third and fourth faces, being substantially concavely-angled, and the remainder of (1) said first and second annuluses faces, and (2) said third and fourth faces being substantially convexly-angled such that said third and fourth faces as opposite end-faces of said third annulus are substantially seated one within the other of said first and second annulus faces as opposing faces in juxtaposition spaced-away relationship exerting both axially-directed and transversely extending repelling forces relative to a longitudinal axis of said elongated shaft whereby said elongated shaft is forcefully suspended against both axial and lateral movement, by outside forces acting on said shaft.

2. A magnetic bearing unit of claim 1, in which relative to a plane extending transversely through said elongated shaft overall average angle defined between said plane and each of said first and second annuluses faces and each of said third and fourth faces being within a range from about 15 degrees to about 35 degrees, whereby repelling magnetic forces are sufficient to resist significantly large axial and transverse forces acting upon said elongated shaft.

3. A magnetic bearing unit of claim 1, in which relative to a plane extending transversely through said elongated shaft, overall average angle defined between said plane and each of said first and second annuluses faces and each of said third and fourth faces is within a range from about 20 degrees to about 25 degrees, whereby repelling magnetic forces are sufficient to resist significantly large axial and transverse forces acting upon said elongated shaft.

4. A magnetic bearing unit of claim 3, in which said first, second and third magnets each is a rare-earth cobalt high energy permanent magnet.

5. A magnetic bearing unit of claim 1, in which said first, second and third magnets each is a rare-earth cobalt high energy permanent magnet.

6. A magnetic bearing unit of claim 4, in which said support structure is non-magnetic material.

7. A magnetic bearing unit of claim 6, including air-turbine flanges extending substantially radially outwardly from and mounted circumscribingly around said third annulus on an outer wall thereof and which said support structure includes a turbine housing designed to channel pressurized air to, against and from said air-turbine flanges and thereby to drive said elongated shaft in rotary motion in the nature of an air turbine, as a dental drill.

8. A magnetic bearing unit of claim 6, in which said elongated shaft extends in opposite directions within annulus aperatures of each of said first and second annuluses, and in which bearings are arranged in circumscribing relationship to said elongated shaft are positioned in the vicinity of an upper end of said first annulus and of a lower end of said second annulus, said bearings being mounted on and supported by said support structure and in spaced-away relationship from said elongated shaft and positioned such that said elongated shaft will press against said bearings prior to said third annulus striking either of said first and second annuluses in the event of sufficient to exceed lateral repelling magnetic forces between said third magnet and each of said first and second magnets.

9. A magnetic bearing unit of claim 1, including air-turbine flanges extending substantially radially outwardly from and circumscribingly around said third annulus from an outer wall thereof, and in which said support structure includes a turbine housing designed to channel pressurized air to, against and from said air-turbine flanges and thereby to drive said elongated shaft in rotary motion in the nature of an air-turbine, as a dental drill, said air-turbine flange being an integral magnetic part of said third annulus.

* * * * *